(12) United States Patent
Demick et al.

(10) Patent No.: US 11,429,934 B2
(45) Date of Patent: Aug. 30, 2022

(54) EXPRESS TRACKING FOR PATIENT FLOW MANAGEMENT IN A DISTRIBUTED ENVIRONMENT

(71) Applicant: LABORATORY CORPORATION OF AMERICA HOLDINGS, Burlington, NC (US)

(72) Inventors: Michael Demick, Wake Forest, NC (US); Mark Wright, Tobaccoville, NC (US)

(73) Assignee: Laboratory Corporation of America Holdings, Burlington, NC (US)

(*) Notice: Subject to any disclaimer, the term of this patent is extended or adjusted under 35 U.S.C. 154(b) by 314 days.

(21) Appl. No.: 16/669,099

(22) Filed: Oct. 30, 2019

(65) Prior Publication Data
US 2020/0134571 A1   Apr. 30, 2020

Related U.S. Application Data

(60) Provisional application No. 62/752,723, filed on Oct. 30, 2018.

(51) Int. Cl.
G06Q 10/10 (2012.01)
G16H 40/20 (2018.01)
(Continued)

(52) U.S. Cl.
CPC ......... *G06Q 10/1095* (2013.01); *G06N 3/08* (2013.01); *G06Q 40/08* (2013.01); *G06V 30/416* (2022.01); *G16H 40/20* (2018.01)

(58) Field of Classification Search
CPC .... G06Q 10/1095; G06Q 40/08; G16H 40/20; G06K 9/00469; G06N 3/08
See application file for complete search history.

(56) References Cited

U.S. PATENT DOCUMENTS

2009/0006439 A1* 1/2009 Joseph ................. G16H 40/20
2011/0288882 A1* 11/2011 Halow .................. G16H 10/60
  705/2

(Continued)

OTHER PUBLICATIONS

Kharraz, "Introducing Zocdoc Insurance Checker: Verify Your Plan Details and Book with Confidence", Available online at: https://www.zocdoc.com/about/blog/company/introducing-zocdoc-insurance-checker/, Oct. 24, 2017, 2 pages.
(Continued)

*Primary Examiner* — Fayyaz Alam
(74) *Attorney, Agent, or Firm* — Kilpatrick Townsend & Stockton LLP

(57) ABSTRACT

The present invention relates to systems and methods of express tracking for patient flow management in a distributed environment. Particularly, aspects are directed to a computer implemented method that includes initiating a check-in process that includes prompting a user to scan an identifier, processing the identifier using a cascade machine-learning architecture comprising of a multi-task convolutional neural network model and a recurrent neural network model to obtain the classification of the identifier and member identification information, determining whether the user is known user based on the member identification information, when the user is a known user, verifying user data saved in the computing system associated with the identifier, once the user data is verified, determining whether the user has a scheduled appointment; and when the user has a scheduled appointment, checking the user in for the scheduled appointment.

18 Claims, 8 Drawing Sheets

(51) Int. Cl.
  *G06N 3/08* (2006.01)
  *G06Q 40/08* (2012.01)
  *G06V 30/416* (2022.01)

(56) References Cited

U.S. PATENT DOCUMENTS

2014/0229194 A1* 8/2014 Brooks .................. G06Q 40/08
                                                            705/2
2015/0227690 A1   8/2015 St. Jacques
2021/0256615 A1* 8/2021 Hayward ................. G06N 3/08

OTHER PUBLICATIONS

Kushal , "Making Sense of Insurance Cards Using Deep Learning", Available online at: https://www.zocdoc.com/about/blog/tech/making-sense-of-insurance-cards-using-deep-learning/, Oct. 24, 2017, pp. 1-6.
PCT/US2019/058875 , "International Search Report and Written Opinion", dated Jan. 29, 2020, 13 pages.
Simonyan et al., "Very Deep Convolutional Networks for Large-Scale Image Recognition", Available Online at: https://arxiv.org/pdf/1409.1556.pdf, Apr. 10, 2015, 14 pages.

* cited by examiner

EXPRESS TRACKING FOR PATIENT FLOW MANAGEMENT IN A DISTRIBUTED ENVIRONMENT

CROSS-REFERENCE TO RELATED APPLICATION

The present application claims the benefit of priority to U.S. Provisional Application No. 62/752,723, filed Oct. 30, 2018, the entire contents of which are incorporated by reference herein for all purposes.

FIELD OF THE INVENTION

The present invention relates to patient flow, and in particular techniques are provided (e.g., a method, a system, non-transitory computer-readable medium storing code or instructions executable by one or more processors) for express tracking of patient flow management in a distributed environment.

BACKGROUND

Patient flow is the movement of patients through a healthcare facility. It involves the medical care, physical resources, and internal systems needed to get patients from the point of admission to the point of discharge while maintaining quality and patient/provider satisfaction. Improving patient flow is a critical component of process management in hospitals and other healthcare facilities. Patient flow is primarily associated with hospitals and doctor's offices, especially with back-ups, overcrowding, and inefficient scheduling. However, patient flow problems are not isolated to hospitals and doctor's offices, patient flow problems also exist in ancillary healthcare services such as radiology centers, medical laboratories, respiratory therapy offices, dialysis centers, chemotherapy centers, urgent care clinics, etc.

Conventional patient flow management systems resemble any complex queueing network in that delays are reduced through: (1) synchronization of work among service stages (e.g., coordination of patient intake, diagnosis processes, medical testing, treatments, and discharge processes), (2) automation of information gathering and data processing, (3) scheduling of resources (e.g., doctors, nurses, technicians, service providers, etc.) to match patterns of arrival, and (4) constant system monitoring (e.g., tracking number of patients waiting by location, diagnostic grouping and acuity) linked to immediate actions. In order to improve upon conventional techniques for managing patient flow, a primary goal for patient flow management systems has been to optimize resource management such as scheduling beds and services for patients, optimize monitoring of the patient flow in real-time, and provide intuitive analysis of incoming data to provide solutions for problems that arise in the patient flow. Although conventional patient flow management systems achieve some success in reducing patient wait times, decreasing costs associated with poor patient flow (e.g., wasted resources), and reducing lost opportunities (e.g., walk-outs), these systems do not typically focus on improving the intake and discharge processes of the patient flow management. Instead, these systems typically focus improvements on activities and processes that occur between the point of admission and the point of discharge and simply rely on a number of software products running on multiple platforms to implement the intake and discharge processes. This ad hoc manner for implementing the intake and discharge processes can lead to bottlenecks in the patient flow, increased costs to maintain the various products and platforms, and increased complexity requiring specialized training on each piece of software. Accordingly, the need exists for improved techniques for patient flow management.

BRIEF SUMMARY

Techniques are provided (e.g., a method, a system, non-transitory computer-readable medium storing code or instructions executable by one or more processors) for express tracking of patient flow management in a distributed environment.

In various embodiments, systems and methods of express tracking are provided for patient flow management in a distributed environment. Particularly, aspects are directed to a computer implemented method that includes initiating a check-in process that includes prompting a user to scan an identifier; determining whether the user is known user based on the identifier; when the user is a known user, verifying user data saved in the computing system associated with the identifier; once the user data is verified, determining whether the user has an outstanding balance for prior services; when the user does not have the outstanding balance, determining whether the user has a scheduled appointment; and when the user has a scheduled appointment, checking the user in for the scheduled appointment.

In some embodiments, the method further comprises when the user is not the known user, initiating a registration process that includes requesting demographic information from the user and prompts the user to accept terms and conditions for scheduling services via the computing system.

In some embodiments, the method further comprises when the user does not have a scheduled appointment or after accepting the terms and conditions for scheduling the services via the computing system, displaying a list of services currently available for appointment, and prompting the user to select one or more services for scheduling; upon receiving the selection of the one or more services, displaying a list of times currently available for having the one or more services performed, and prompting the user to select a time for scheduling; and upon receiving the selection of the time, generating an appointment for the services at the selected time.

In some embodiments, the method further comprises when the user does have the outstanding balance, prompting the user to pay the outstanding balance or a portion of the outstanding balance.

In various embodiments, a method is provided comprising: initiating, by a computing system in a distributed environment, a check-in process that includes prompting a user to scan an identifier; receiving, by the computing system, image data from the scan of the identifier; extracting, by a first convolutional layer of a multi-task convolutional neural network model, a first set of features from the image data for a first piece of information on the identifier, wherein the first set of features are specific to a first task of classifying the identifier; extracting, by a second convolutional layer of the multi-task convolutional neural network model, a second set of features from the image data, wherein the second set of features are specific to a task of predicting a location of a second piece of information on the identifier; classifying, by a first fully connected layer of the multi-task convolutional neural network model, the identifier based on the first set of features and the second set of features; predicting, by a second fully connected layer of the multi-task convolutional neural network model, the location of the second piece of information on the identifier based on the first set of features and the second set of features; extracting, by the computing system, image data pertaining to the second piece of information based on the predicted location of the second piece of information on the identifier; generating, by a recurrent neural network model, a sequence of alphanumeric characters from the image data pertaining to the second piece of information; outputting, by the multi-task convolutional neural network, the classification of the identifier based on the first piece of information; and outputting, by the recurrent neural network model, the second piece of information as the sequence of generated alphanumeric characters.

In some embodiments, the identifier is an insurance card, the first piece of information is an insurance provider, and the second piece of information is a member identifier.

In some embodiments, the method further comprises: determining, by the computing system, whether the user is known user based on the second piece of information; when the user is a known user, verifying, by the computing system, user data saved in the computing system associated with the identifier; once the user data is verified, determining, by the computing device, whether the user has an outstanding balance for prior services; when the user does not have the outstanding balance, determining, by the computing device, whether the user has a scheduled appointment; and when the user has a scheduled appointment, checking the user in for the scheduled appointment.

In some embodiments, the method further comprises when the user is not the known user, initiating, by the computing system, a registration process that includes requesting demographic information from the user and prompts the user to accept terms and conditions for scheduling services via the computing system.

In some embodiments, the method further comprises: when the user does not have a scheduled appointment or after accepting the terms and conditions for scheduling the services via the computing system, displaying, by the computing system, a list of services currently available for appointment, and prompting the user to select one or more services for scheduling; upon receiving the selection of the one or more services, displaying, by the computing system, a list of times currently available for having the one or more services performed, and prompting the user to select a time for scheduling; and upon receiving the selection of the time, generating, by the computing system, an appointment for the services at the selected time.

In some embodiments, the method further comprises when the user does have the outstanding balance, prompting, by the computing device, the user to pay the outstanding balance or a portion of the outstanding balance.

In some embodiments, a method is provided that comprises initiating, by a computing system in a distributed environment, a check-in process that includes prompting a user to scan an identifier; determining, by the computing system, whether the user is known user based on the identifier; when the user is not the known user, initiating, by the computing system, a registration process that includes requesting demographic information from the user and prompts the user to accept terms and conditions for scheduling services via the computing system. The requesting includes prompting the user to scan in their insurance card. The method further comprises receiving, by the computing system, image data from the scan of the insurance card; extracting, by a first convolutional layer of a multi-task convolutional neural network model, a first set of features from the image data for a first piece of information on the insurance card, wherein the first set of features are specific to a first task of classifying the insurance card; extracting, by a second convolutional layer of the multi-task convolutional neural network model, a second set of features from the image data, wherein the second set of features are specific to a task of predicting a location of a second piece of information on the insurance card; classifying, by a first fully connected layer of the multi-task convolutional neural network model, the insurance card based on the first set of features and the second set of features; predicting, by a second fully connected layer of the multi-task convolutional neural network model, the location of the second piece of information on the insurance card based on the first set of features and the second set of features; extracting, by the computing system, image data pertaining to the second piece of information based on the predicted location of the second piece of information on the insurance card; generating, by a recurrent neural network model, a sequence of alphanumeric characters from the image data pertaining to the second piece of information; outputting, by the multi-task convolutional neural network, the classification of the identifier based on the first piece of information; and outputting, by the recurrent neural network model, the second piece of information as the sequence of generated alphanumeric characters.

In some embodiments, a system is provided that includes one or more data processors and a non-transitory computer readable storage medium containing instructions which, when executed on the one or more data processors, cause the one or more data processors to perform part or all of one or more methods disclosed herein.

In some embodiments, a computer-program product is provided that is tangibly embodied in a non-transitory machine-readable storage medium and that includes instructions configured to cause one or more data processors to perform part or all of one or more methods disclosed herein.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims

BRIEF DESCRIPTION OF THE DRAWINGS

The present invention will be better understood in view of the following non-limiting figures, in which.

DETAILED DESCRIPTION

I. Patient Flow Management System

In various embodiments, a system of express tracking for patient flow management is provided in a distributed environment. As used herein, a "distributed environment" is a computer networking scheme in which multiple software components (such as bill payment services, registration services, data collection services, security services, etc.) are integrated to work closely toward well-developed objectives. These objectives may include the intake and discharge processes of a patient flow in a medical facility such as a medical laboratory.

Figure 1:
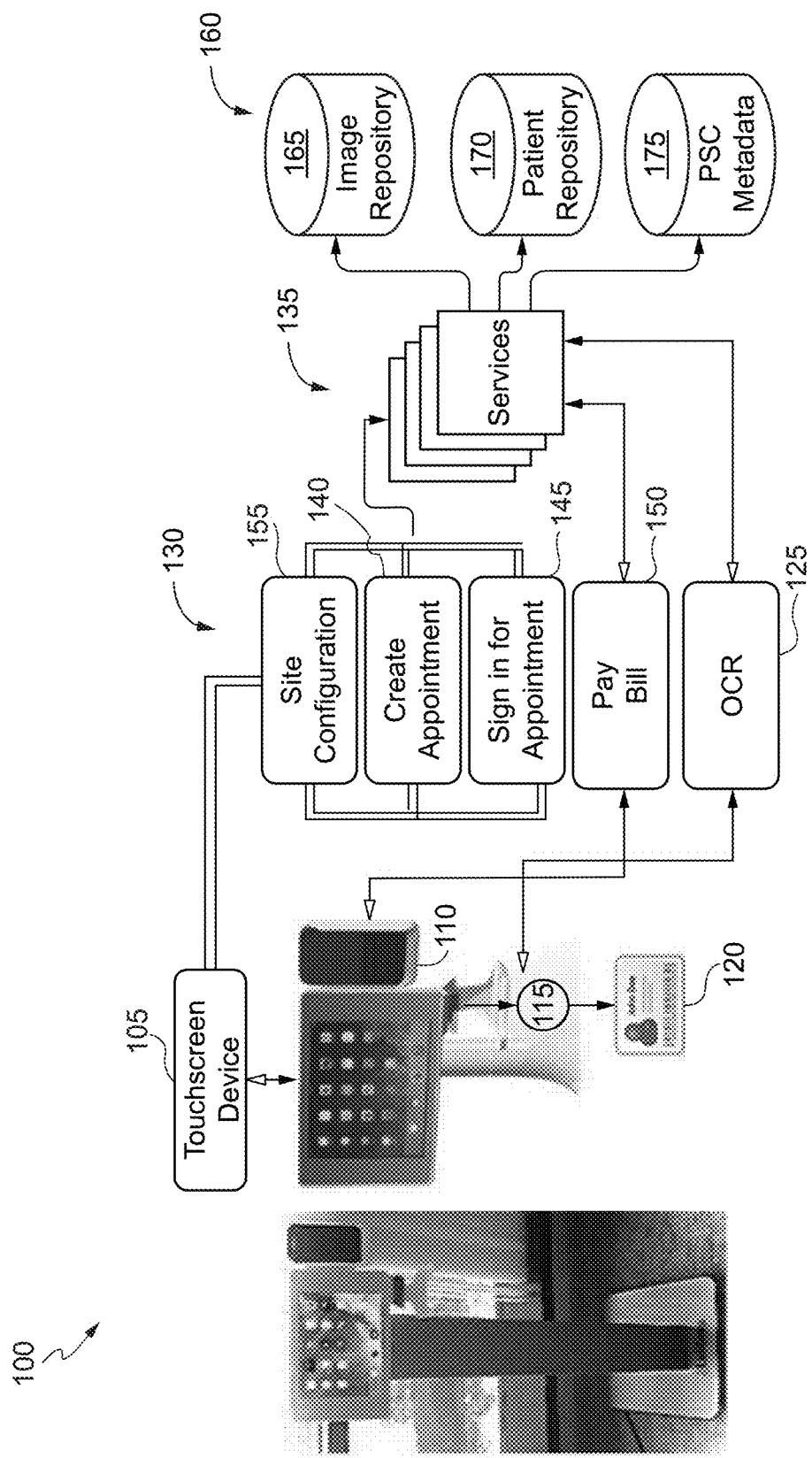
FIG. 1 shows an exemplary patient flow management system according to various embodiments.

FIG. 1 is an illustrative patient flow management system 100 of express tracking for patient flow management implemented as various embodiments. In some embodiments, the system 100 includes an input device 105 such as a touch screen configured to display a web-based interface such as a website with a graphical user interface (GUI) for a user to interact and perform one or more processes associated with the patient flow. For example, a user may use the input device 105 to input their name to schedule an appointment or sign-in for an appointment. In some embodiments, the system 100 includes a card reader 110 to process invoice payments. In some embodiments, the system includes an integrated camera 115 for image capture. For example the camera may be used to scan various documents and identifiers 120 such as QR codes, PDF417 codes, driver's licenses, bar codes, insurance cards, etc. In certain embodiments, the integrated camera 115 includes or is in communication with an optical character recognition (OCR) module 125 that allows it to extract text from captured images. In certain embodiments, the integrated camera 115 includes a tray such that the documents and identifiers can be positioned near the integrated camera 115 for capture.

In various embodiments, the system 100 includes one or more modules 130 (e.g., software and/or hardware configured for providing one or more services) for execution of processes and providing functionality as described herein including providing services 135. In some embodiments, the system 100 includes an appointment module 140 to allow a user to create an appointment. For example, the user may create an appointment for laboratory testing. In certain embodiments, the appointment module 140 includes a set of services (e.g., a scheduler, a service catalogue, a notification provider, etc.) for creating the appointment. In some embodiments, the system 100 includes a sign-in module 145 to allow a user to sign-in to an appointment. For example, the user may sign-in to an appointment previously created for laboratory testing. In certain embodiments, the sign-in module 145 includes a set of services (e.g., scanning a driver's license, obtaining insurance information, user authentication, etc.) for signing into the appointment. In some embodiments, the system 100 includes bill payment module 150 to allow a user to pay a bill. For example, the user may pay a bill for prior service such as laboratory testing. In certain embodiments, the bill payment module 150 includes a set of services (e.g., a scanning a credit card or payment method, invoice generation, a notification provider, accounting manager, etc.) for paying a bill. In some embodiments, the system 100 further includes a device configuration module 155 for configuring the various devices such as the integrated camera 115 and card reader 110. In certain embodiments, the device configuration module 155 includes a set of services (e.g., a device driver manager, a network manager, an install wizard, etc.) for configuring the various devices.

In some embodiments, the system 100 includes various storage devices 160 such as databases or repositories for storing data used to execute patient flow processes or obtained/created during the patient flow processes. In some embodiments, the system 100 includes an image repository 150 for storing images obtained via the camera. For example, the image repository 150 repository may store images of the driver's licenses and insurance cards for use in later processing steps including model training, machine learning analysis, auditing, and verification. In some embodiments, the system 100 includes a patient repository 155 for storing patient information or meta-data. For example, the patient repository 155 repository may store a profile for the patient including their name, contact information, billing information, and medical history for use in later processing steps including bill payment processes, appointment scheduling, verification, and tracking. In some embodiments, the system includes a site configuration repository 160 for storing site configuration information or meta-data used in driving input and the display of data on the website. For example, the site configuration repository 160 repository may store information for editing the website and GUI components of the website, including security settings such as authentication and authorization policies, URL redirects, active status of various GUI components, page layouts, login or registration settings, etc.

In various embodiments, the system 100 includes a custom housing 165 with the fully integrated computing system having the aforementioned hardware/software for patient flow management. However, it should be understood that the above example is merely illustrative. The hardware/software for patient flow management could be provided in a distributed environment such as a cloud and accessed via a mobile device application. For instance, a user (e.g., a patient) may access a patient flow management application on their own computing device (e.g., a mobile device), log into a personalized account (e.g., using account authentication/authorization management solutions) and perform any of the aforementioned services (e.g., schedule an appointment, pay a bill, sign-in for an appointment, etc.). The one or more modules 130 (e.g., software and/or hardware configured for providing one or more services) for execution of processes and providing functionality as described herein including providing services 135 may be provided within the application, provided within the distributed environment, or a combination thereof. In this way, a user can have access to the services 135 at any time and location.

Figure 2:
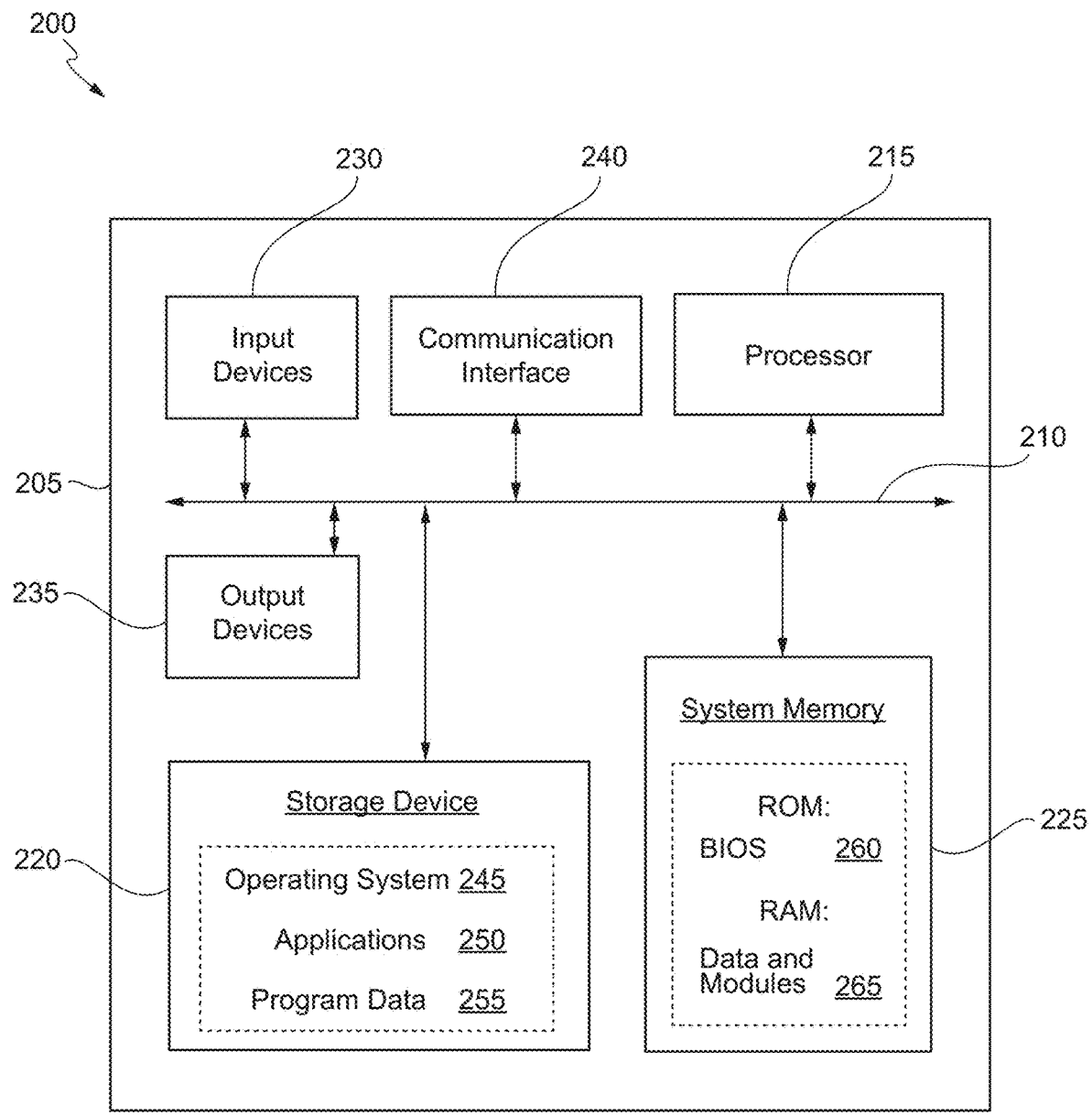
FIG. 2 shows an illustrative architecture of a computing system implemented according to various embodiments.

FIG. 2 is an illustrative architecture of a computing system 200 implemented as various embodiments, e.g., the patient flow management system 100 of FIG. 1. For example, the computing system 200 may be part of a stand-alone kiosk, a user terminal, an administrators terminal, a mobile device, etc. The computing system 200 is only one example of a suitable computing system and is not intended to suggest any limitation as to the scope of use or functionality of the present invention. Also, computing system 200 should not be interpreted as having any dependency or requirement relating to any one or combination of components illustrated in computing system 200.

As shown in FIG. 2, computing system 200 includes a computing device 205. The computing device 205 can be resident on a network infrastructure such as within a distributed environment (for example a cloud environment). In some embodiments, a cloud environment may provide one or more services for patient flow management in a distributed environment. The computing device 205 may include a bus 210, processor 215, a storage device 220, a system memory (hardware device) 225, one or more input devices 230, one or more output devices 235, and a communication interface 240.

The bus 210 permits communication among the components of computing device 205. For example, bus 610 may be any of several types of bus structures including a memory bus or memory controller, a peripheral bus, and a local bus using any of a variety of bus architectures to provide one or more wired or wireless communication links or paths for transferring data and/or power to, from, or between various other components of computing device 205.

The processor 215 may be one or more conventional processors, microprocessors, or specialized dedicated processors that include processing circuitry operative to interpret and execute computer readable program instructions, such as program instructions for controlling the operation and performance of one or more of the various other components of computing device 205 for implementing the functionality, steps, and/or performance of the present invention. In certain embodiments, processor 215 interprets and executes the processes, steps, functions, and/or operations of the present invention, which may be operatively implemented by the computer readable program instructions. For example, processor 215 can obtain patient data, e.g., query and/or otherwise obtain or generate a profile data and medical data for a patient. The processor 215 can further develop an interaction network model algorithmically using the data and identify potential patient flow issues. In embodiments, the patient data, the interaction network model, and the potential patient flow issues developed by the processor 215 can be stored in the storage device 220.

The storage device 220 may include removable/non-removable, volatile/non-volatile computer readable media, such as, but not limited to, non-transitory machine readable storage medium such as magnetic and/or optical recording media and their corresponding drives. The drives and their associated computer readable media provide for storage of computer readable program instructions, data structures, program modules and other data for operation of computing device 205 in accordance with the different aspects of the present invention. In embodiments, storage device 220 may store operating system 245, application programs 250, and program data 255 in accordance with aspects of the present invention.

The system memory 225 may include one or more storage mediums, including for example, non-transitory machine readable storage medium such as flash memory, permanent memory such as read-only memory ("ROM"), semi-permanent memory such as random access memory ("RAM"), any other suitable type of non-transitory storage component, or any combination thereof. In some embodiments, an input/output system 260 (BIOS) including the basic routines that help to transfer information between the various other components of computing device 205, such as during start-up, may be stored in the ROM. Additionally, data and/or program modules 265, such as at least a portion of operating system 245, program modules, application programs 250, and/or program data 255, that are accessible to and/or presently being operated on by processor 215, may be contained in the RAM. In embodiments, the program modules 265 and/or application programs 250 can comprise an appointment module, sign-in module, configuration module, a query device or web crawler, algorithms such as Dikstra's shortest paths, direct connections, a grow algorithm to build the interaction network model, a comparison tool, and one or more databases, for example, of known appointments, patients, and medical resources such as medical technologists, which provides the instructions and data for execution of the processor 215.

The one or more input devices 230 may include one or more mechanisms that permit an operator to input information to computing device 205, such as, but not limited to, a touch pad, dial, click wheel, scroll wheel, touch screen, one or more buttons (e.g., a keyboard), mouse, game controller, track ball, microphone, camera, proximity sensor, light detector, motion sensors, biometric sensor, and combinations thereof. The one or more output devices 235 may include one or more mechanisms that output information to an operator, such as, but not limited to, audio speakers, headphones, audio line-outs, visual displays, antennas, infrared ports, tactile feedback, printers, or combinations thereof.

The communication interface 240 may include any transceiver-like mechanism (e.g., a network interface, a network adapter, a modem, or combinations thereof) that enables computing device 605 to communicate with remote devices or systems, such as a mobile device or other computing devices such as, for example, a server in a networked environment, e.g., cloud environment. For example, computing device 205 may be connected to remote devices or systems via one or more local area networks (LAN) and/or one or more wide area networks (WAN) using communication interface 240.

As discussed herein, computing system 200 may be configured to obtain various data from a user, check-in a user, check-in a user without a prior appointment, generate an appointment for a user, and identify potential issues with the patient workflow. In particular, computing device 205 may perform tasks (e.g., process, steps, methods and/or functionality) in response to processor 215 executing program instructions contained in non-transitory machine readable storage medium, such as system memory 225. The program instructions may be read into system memory 225 from another computer readable medium (e.g., non-transitory machine readable storage medium), such as data storage device 220, or from another device via the communication interface 240 or server within or outside of a cloud environment. In embodiments, an operator may interact with computing device 205 via the one or more input devices 230 and/or the one or more output devices 235 to facilitate performance of the tasks and/or realize the end results of such tasks in accordance with aspects of the present invention. In additional or alternative embodiments, hardwired circuitry may be used in place of or in combination with the program instructions to implement the tasks, e.g., steps, methods and/or functionality, consistent with the different aspects of the present invention. Thus, the steps, methods and/or functionality disclosed herein can be implemented in any combination of hardware circuitry and software.

II. Techniques for Managing Patient Flow

Figure 3:
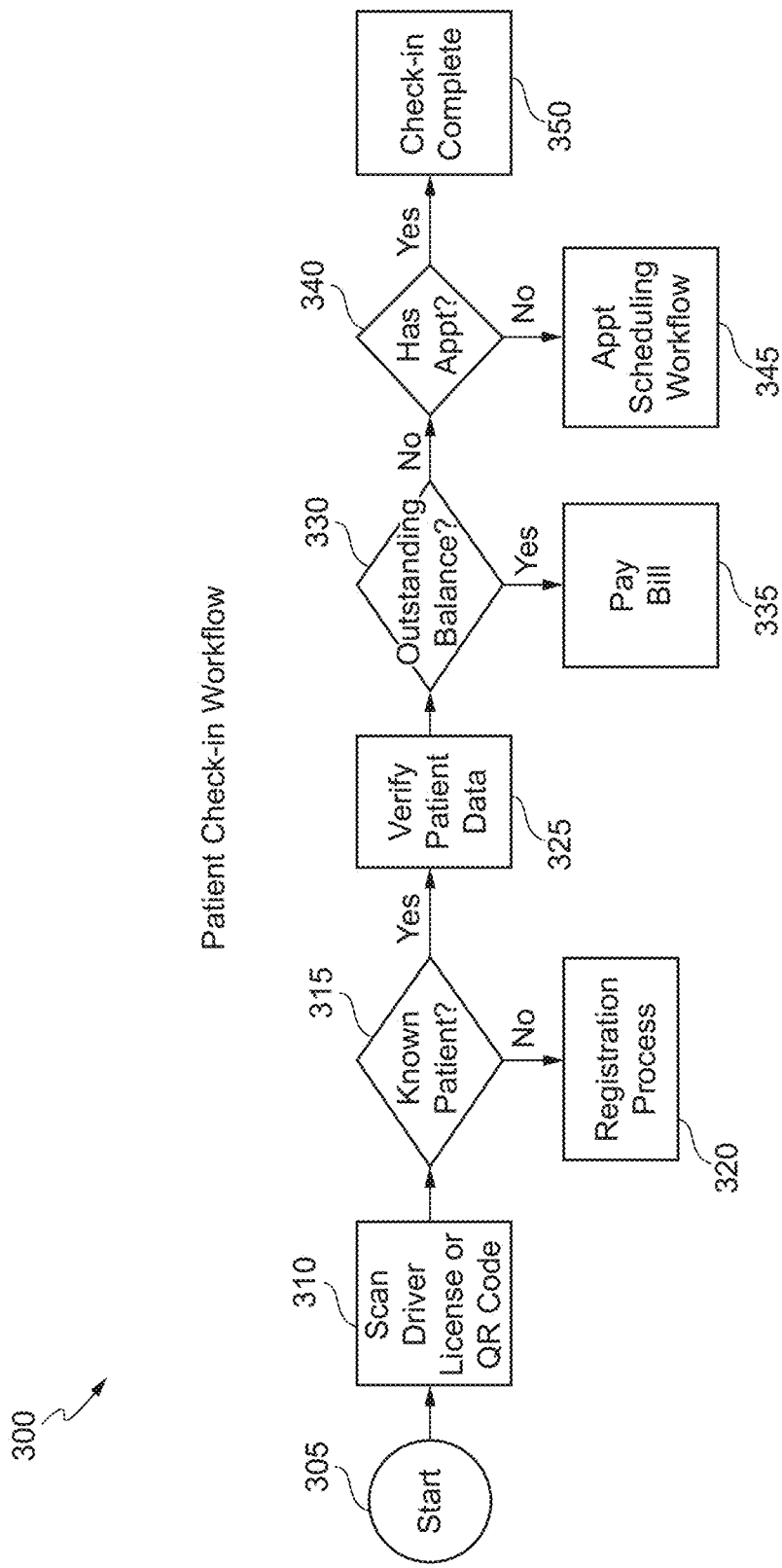
FIG. 3 shows an exemplary flow for patient check-in according to various embodiments.
Figure 4:
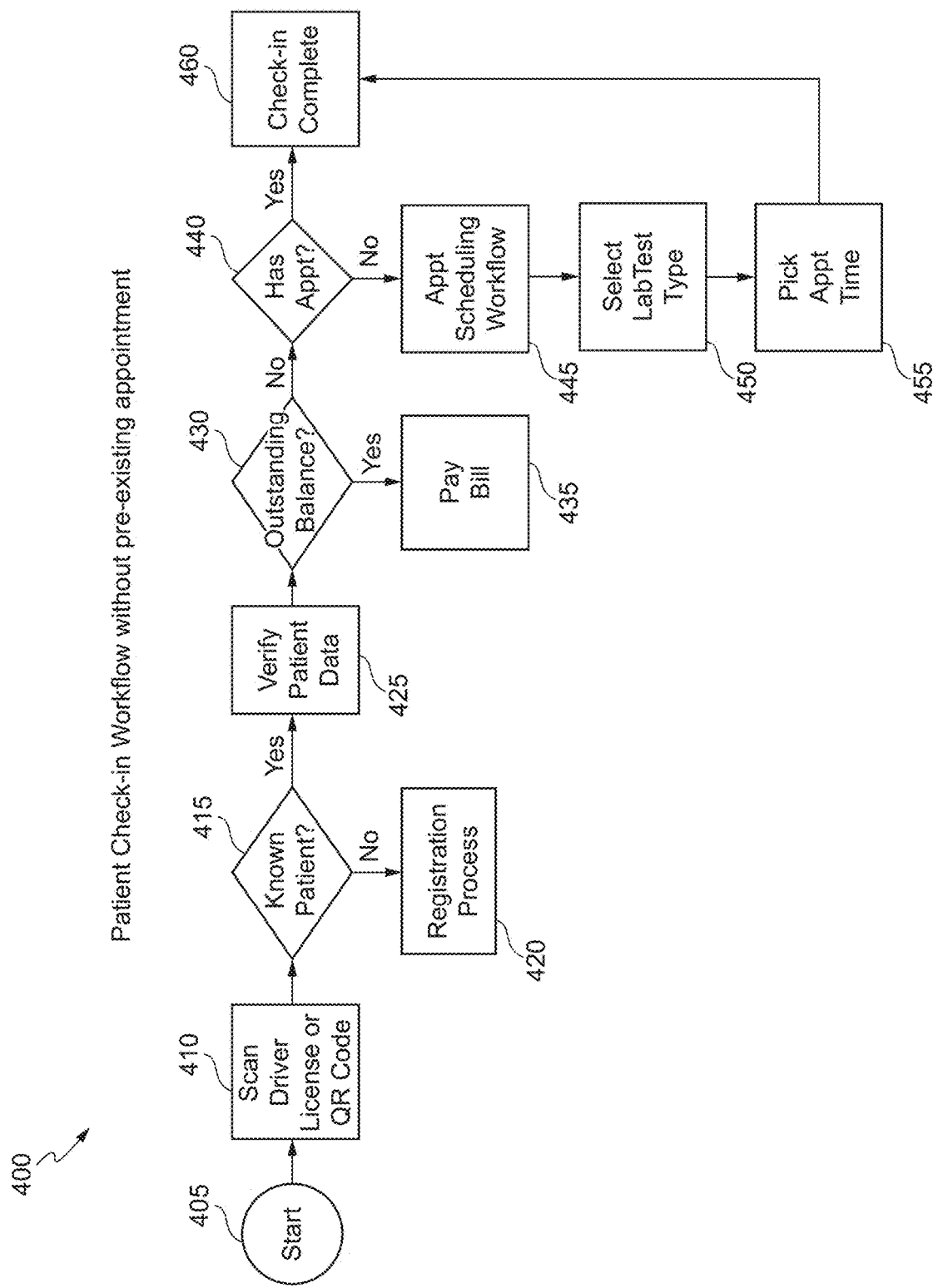
FIG. 4 shows an exemplary flow for patient check-in without a pre-existing appointment according to various embodiments.
Figure 5:
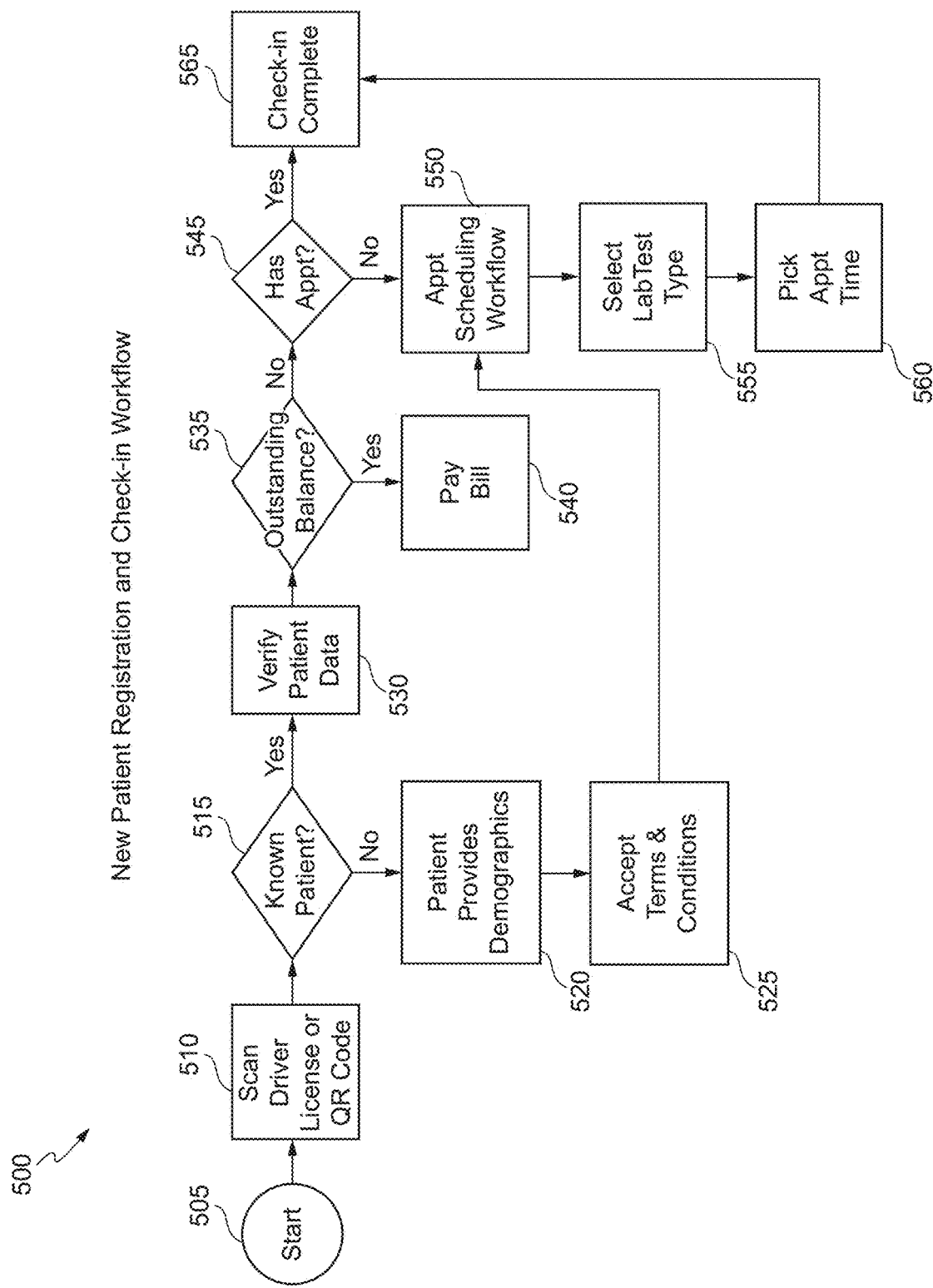
FIG. 5 shows an exemplary flow for new patient registration and check-in according to various embodiments.

FIGS. 3, 4, and 5 depict simplified flowcharts depicting processing performed for patient flow management according to various embodiments. The steps of FIGS. 2, 3, and 4 may be implemented in the system environment of FIGS. 1 and 2, for example. As noted herein, the flowcharts of FIGS. 3, 4, and 5 illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical functions. It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combination of blocks in the block diagrams and/or flowchart illustration, can be implemented by special purpose hardware-based systems that perform the specified functions or acts, or combinations of special purpose hardware and computer instructions.

FIG. 3 depicts a simplified flowchart 300 illustrating a process for patient check-in. The process depicted in FIG. 3 starts at step 305. At step 310, the system initiates a check-in process that includes prompting a user to scan an identifier such as a driver's license, insurance card, or QD code. The system obtains image capture data from the scan of the identifier. Optionally, the system uses OCR to derive text from the image capture data. At step 315, the system determines whether the user is a known user based on the identifier obtained in step 305. If the user is not a known user then process continues at step 320 where a registration process is initiated (see, e.g., FIG. 5). If the user is a known user, then the process continues at step 325 where patient data is verified. In some embodiments, verification of patient data may include the system displaying patient data (e.g., most recent contact information, medical history, etc.) stored in the system to the user and requesting the user to review the data and confirm the accuracy of the data in the system. In other embodiments, the verification of patient data may include the system using the comparator to compare data obtained from the scanning of the identifier and any other documents to data (e.g., most recent contact information, medical history, etc.) stored in the system about the user to verify the accuracy of the data in the system automatically. Optionally, if any data is not verified the system may prompt the user to edit or correct the data. At step 330, the system determines whether the known user has an outstanding balance based on invoice/balance data in the system associated with the know user. If there is an outstanding balance, then the process continues at step 335 where user is prompted to pay the outstanding balance or a portion thereof. If there is no outstanding balance, then the process continues at step 340 where a determination is made as to whether the user has a current appointment scheduled. If there is no appointment currently scheduled, then the process continues at step 345 where a scheduling process is initiated (see, e.g., FIG. 4). If there is an appointment currently scheduled, then the process continues at step 350 where the user is checked-in for the scheduled appointment. In some embodiments, checking in the user includes the system flagging the user as checked-in and updating other systems on the current status of the appointment. For example, updating, resource scheduling software that the user is now waiting for a service such as medical testing.

FIG. 4 depicts a simplified flowchart 400 illustrating a process for patient check-in without pre-existing appointment. The process depicted in FIG. 4 starts at step 405. At step 410, the system initiates a check-in process that includes prompting a user to scan an identifier such as a driver's license, insurance card, or QD code. The system obtains image capture data from the scan of the identifier. Optionally, the system uses OCR to derive text from the image capture data. At step 415, the system determines whether the user is a known user based on the identifier obtained in step 405. If the user is not a known user then process continues at step 420 where a registration process is initiated (see, e.g., FIG. 5). If the user is a known user, then the process continues at step 425 where patient data is verified. In some embodiments, verification of patient data may include the system displaying patient data (e.g., most recent contact information, medical history, etc.) stored in the system to the user and requesting the user to review the data and confirm the accuracy of the data in the system. In other embodiments, the verification of patient data may include the system using the comparator to compare data obtained from the scanning of the identifier and any other documents to data (e.g., most recent contact information, medical history, etc.) stored in the system about the user to verify the accuracy of the data in the system automatically. Optionally, if any data is not verified the system may prompt the user to edit or correct the data. For example, the user may be prompted to scan or rescan their insurance card.

At step 430, the system determines whether the known user has an outstanding balance based on invoice/balance data in the system associated with the know user. If there is an outstanding balance, then the process continues at step 435 where user is prompted to pay the outstanding balance or a portion thereof. If there is no outstanding balance, then the process continues at step 440 where a determination is made as to whether the user has a current appointment scheduled. If there is no appointment currently scheduled, then the process continues at step 445 where a scheduling process is initiated. At step 450, the system displays a list of services (e.g., various lab tests) currently available for appointment, and prompts a user to select one or more services for scheduling. Upon receiving the selection of the one or more services, at step 455, the system displays a list of times currently available for having those services performed (e.g., having blood work taken for a lab test), and prompts a user to select a time for scheduling. Once the services and time and selected, the system generates an appointment for the services at the selected time and stores the appointment in the system. The appointment is stored with a link to the user data. Once the appointment is scheduled or if the appointment was previously scheduled, then the process continues at step 460 where the user is checked-in for the scheduled appointment. In some embodiments, checking in the user includes the system flagging the user as checked-in and updating other systems on the current status of the appointment. For example, updating, resource scheduling software that the user is now waiting for a service such as blood work for laboratory testing.

FIG. 5 depicts a simplified flowchart 500 illustrating a process for patient check-in. The process depicted in FIG. 5 starts at step 505. At step 510, the system initiates a check-in process that includes prompting a user to scan an identifier such as a driver's license, insurance card, or QD code. The system obtains image capture data from the scan of the identifier. Optionally, the system uses OCR to derive text from the image capture data. At step 515, the system determines whether the user is a known user based on the identifier obtained in step 505. If the user is not a known user then process continues at step 520 where a registration process is initiated. In some embodiments, the registration process includes requesting demographic information from the user. In certain embodiments, the demographic information is requested from the user using a configurable template of predetermined questions intended to prompt responses to obtain predetermined demographic information. For example, requesting the user's name and address, medical history, contact information, medical insurance, etc. In some instances, the registration processes includes prompting the user to scan in their insurance card, and receiving image data from the scan of the insurance card. At step, 525, the system prompts the user to accept the terms and conditions for scheduling services via the system and having service provided by the medical facility. Upon acceptance of the terms and conditions, the user is forwarded by the system to an appointment scheduling workflow at step 550.

If the user is a known user, then the process continues at step 530 where patient data is verified. In some embodiments, verification of patient data may include the system displaying patient data (e.g., most recent contact information, medical history, etc.) stored in the system to the user and requesting the user to review the data and confirm the accuracy of the data in the system. In other embodiments, the verification of patient data may include the system using the comparator to compare data obtained from the scanning of the identifier and any other documents to data (e.g., most recent contact information, medical history, etc.) stored in the system about the user to verify the accuracy of the data in the system automatically. Optionally, if any data is not verified the system may prompt the user to edit or correct the data. At step 535, the system determines whether the known user has an outstanding balance based on invoice/balance data in the system associated with the know user. If there is an outstanding balance, then the process continues at step 540 where user is prompted to pay the outstanding balance or a portion thereof. If there is no outstanding balance, then the process continues at step 545 where a determination is made as to whether the user has a current appointment scheduled. If there is no appointment currently scheduled, then the process continues at step 550 where a scheduling process is initiated. At step 555, the system displays a list of services (e.g., various lab tests) currently available for appointment, and prompts a user to select one or more services for scheduling. Upon receiving the selection of the one or more services, at step 560, the system displays a list of times currently available for having those services performed (e.g., having blood work taken for a lab test), and prompts a user to select a time for scheduling. Once the services and time and selected, the system generates an appointment for the services at the selected time and stores the appointment in the system. The appointment is stored with a link to the user data. Once the appointment is scheduled or if the appointment was previously scheduled, then the process continues at step 565 where the user is checked-in for the scheduled appointment. In some embodiments, checking in the user includes the system flagging the user as checked-in and updating other systems on the current status of the appointment. For example, updating, resource scheduling software that the user is now waiting for a service such as blood work for laboratory testing.

III. Machine-Learning Techniques for Insurance Card Optical Character Recognition Sub-System Insurance cards lack any standards guiding their visual layout, the type and placement of data, as well as the content and structure of insurance data itself. Because of this, there is enormous variability amongst insurance cards, both across insurance providers and within a single provider. New insurance cards are regularly issued, re-issued and changed which, when combined with the absence of governing standards further magnifies this variability over time.

Conventional established methods for electronically extracting insurance card data rely on 'templates' which indicate where data is located on a specific type of card. These templates are manually created and maintained for each known variation of insurance card, meaning a permanent and substantial effort is needed for them to function. These template-based extraction methods are dependent on correct identification of a card, i.e. which variation of card it is, to determine which template to apply against a card. However, the variability problem means the identification, in order to apply the correct template, must first examine a card's contents to determine which type it might be. Traditional OCR (optical data recognition) is often used for this identification problem. In this approach, OCR is used, with varying accuracy, to 'read' the text from an image and convert it to a string of unstructured textual data. Once the raw text is extracted, in this template-based method, logic is applied to the text to attempt to classify the card amongst the known variants using deterministic logic. Typically, the logic is based on the presence of one or many textual keyword or other linguistic clues. Once a card has been through a logical classification and a template applied, an image editing process is employed to cut the sections of interest from the image and using traditional OCR capture the values for the sections (fields).

The card variability problem ensures that deterministic logic to classify a particular card will necessarily result in a high rate of inaccuracy. The card variability problem ensures that manually creating and deploying templates for every card variation as they come into public usage is slow, laborious and backward leading, leading necessarily insure a high rate of inaccuracy. Card images that are misaligned in any way may be unable to allow a rigid template to be successfully applied. These conventional processes are both human labor and computing intensive, resulting in slow performance, and high expense.

To address these limitations and problems, machine-learning techniques disclosed herein can be used for insurance card recognition to gather insurance information from a user during any of the aforementioned patient flow management processes. In various embodiments, annotated insurance cards are used to generate a Convolutional Neural Net (CNN) with a multi-task architecture. A first CNN model task classifies a card based on Insurance Provider. This task results in high accuracy and is not based on predetermined logic nor impacted by misaligned or otherwise imperfect images. A second CNN model task predicts the location (coordinates) of the relevant data in the card image, e.g. "Member ID". The coordinates are used to cut the value from the card. The cut value from the card is input into a second neural net model of the type Recurrent Neural Network (RNN), trained on alphanumeric characters, which converts the cut image field into usable, known text which high accuracy. Advantageously, the entire insurance recognition process is highly compute efficient and completes on standard hardware on average 300× faster than the conventional methods. Moreover, these techniques are able to consume new card examples into the training set and generate updated models automatically. This continuous learning capability effectively offsets the overall card variance problem. These techniques do not require regular investments in labor to generate card templates and deterministic logic, resulting in a vastly less expensive and vastly more durable, flexible and efficient solution to electronic insurance card data extraction.

Figure 6:
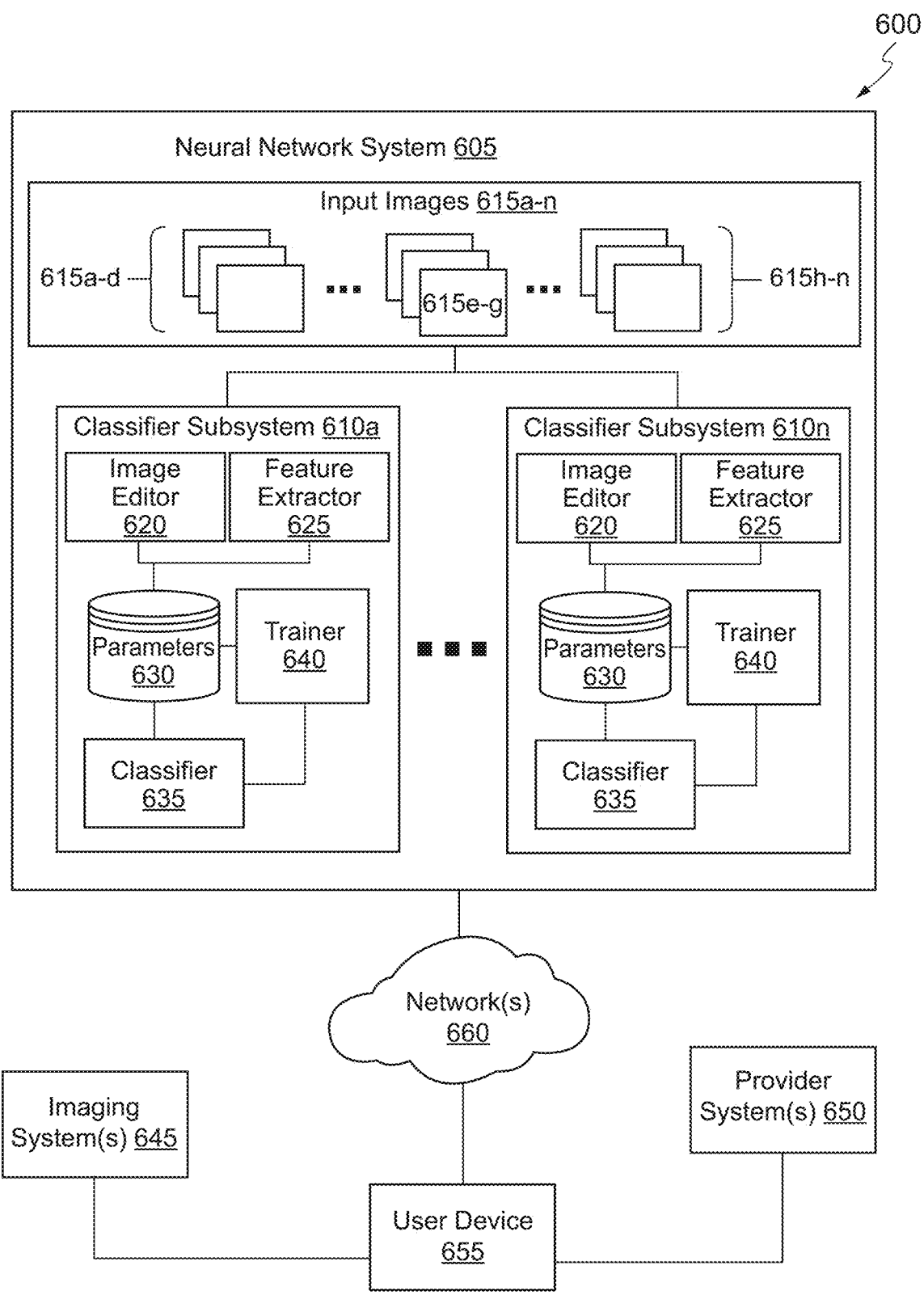
FIG. 6 shows an example computing environment for automated insurance card recognition using a neural network according to various embodiments.

FIG. 6 illustrates an example computing environment 600 for electronic insurance card data extraction using neural networks according to various embodiments. The computing environment 600 can include a neural network system 605 to train and execute CNN models, RNN models, or a combination thereof. More specifically, the neural network system 605 can include classifier subsystems 610a-n that can train their respective CNN models and/or RNN models. In some embodiments, each CNN model and/or RNN model corresponding to the classifier subsystems 610a-n is separately trained based on a set of input image elements 615a-n. In some embodiments, each of the input image elements 615a-n include a digital image depicting an insurance card. Each of the input image elements 615a-n can correspond to a single insurance card of a single patient for which underlying image data corresponding to the insurance card was collected. The input image elements 615a-n can include one or more training input image elements 615a-d, validation input image elements 615e-g, and unlabeled input image elements 615h-n. It will be appreciated that input image elements corresponding to the training, validation and unlabeled groups need not be accessed at a same time. For example, an initial training and validation input image elements may first be accessed and used to train a model, and unlabeled input image elements may be subsequently accessed or received (e.g., at a single or multiple subsequent times).

In some instances, the CNN models and/or RNN models can be trained using supervised training, and each of the training input image elements 615a-d and the validation input image elements 615e-g can be associated with one or more labels that identify a "correct" interpretation of a an insurance provider and/or member ID from the insurance card. In some instances, the CNN models and/or RNN models can be trained using unsupervised training, and each of the training input image elements 615a-d and the validation input image elements 615e-g need not be associated with one or more labels. The CNN models and/or RNN models can be trained using the training input image elements 615a-d (and the validation input image elements 615e-g to monitor training progress), a loss function and/or a gradient descent method. In instances for which an input image data element comprises multiple features, for example, insurance provider and member ID, which are to be used in a multi-task architecture for various classifications and predictions, each of a set of the CNN models and/or RNN models can be trained to process the image data corresponding to the specific feature or task (e.g., a first set of the CNN models and/or RNN models can be trained on the training input image elements 615a-d to classify an insurance card based on an insurance provider and a second set of the CNN models and/or RNN models can be trained on the training input image elements 615a-d to predict a location of relevant data in the card such as member ID).

In some embodiments, the classifier subsystems 610a-n include an image editor 620, feature extractor 625, a parameter data store 630, a classifier 635, and a trainer 640, which are collectively used to train the CNN models and/or RNN models based on image data (e.g., the training input image elements 615a-d) and optimizing the parameters of the CNN models and/or RNN models during supervised or unsupervised training. In some embodiments, the classifier subsystem 610a-n accesses training data from the training input image elements 615a-d at the input layers. The image editor 620 may pre-process the training data to edit the training input image elements 615a-d (e.g., crop, resize, de-skew, rotate, enhance, etc.) to generate modified image elements 615a-d. The feature extractor 625 extracts relevant features (e.g., edges or sides of the card, rotation of the card, quality of the card, pixel data, etc.) detected within the input image elements 615a-d or modified input image elements 615a-d. The classifier 635 can receive the extracted features and transform the features, in accordance with weights associated with a set of hidden layers in the CNN models and/or RNN models, into one or more output classifiers that classify an insurance card based on relevant information such as insurance provider, predict a location of relevant information on an insurance card such as member ID, predict text or strings of alphanumeric data on an insurance card, or a combination thereof. The trainer 640 may use training data corresponding to the training input image elements 615a-d to train the feature extractor 625 and/or the classifier 635 by facilitating learning one or more parameters. For example, the trainer 640 may use a backpropagation techniques to facilitate learning of weights associated with a set of hidden layers of the CNN models and/or RNN models used by the classifier 635. The backpropagation may use, for example, a stochastic gradient descend (SGD) algorithm to cumulatively update the parameters of the hidden layers. Learned parameters may include, for instance, weights, biases, and/or other hidden layer-related parameters, which can be stored in the parameter data store 630.

An ensemble of trained CNN models and/or RNN models can be deployed to process unlabeled input image elements 615h-n to classify an insurance card based on relevant information such as insurance provider, predict a location of relevant information on an insurance card such as member ID, predict text or strings of alphanumeric data on an insurance card, or a combination thereof. More specifically, a trained version of the feature extractor 625 may generate a feature representation of an unlabeled input image element, which can then be processed by a trained version of the classifier 635. In some embodiments, image features can be extracted from the unlabeled input image elements 615h-n based on one or more convolutional blocks, convolutional layers, residual blocks, or pyramidal layers that leverage dilation of the CNN models in the classifier subsystems 610a-n. The features can be organized in a feature representation, such as a feature vector of the image. The CNN models and/or RNN models can be trained to learn the feature types based on classification and subsequent adjustment of parameters in the hidden layers, including fully connected layers of the CNN models and/or RNN models. In some embodiments, the image features extracted by the convolutional blocks, convolutional layers, residual blocks, or pyramidal layers include feature maps that are matrix of values that represent one or more portions of the insurance card images at which one or more image processing operations have been performed (e.g., edge detection, sharpen image resolution). These feature maps may be flattened for processing by a fully connected layer of the CNN models and/or RNN models, which outputs a feature classification, a location of relevant data on the insurance card, a translation of pixel data to text or strings of alphanumeric data, or a combination thereof.

At least part of the training input image elements 615a-d, the validation input image elements 615e-g and/or the unlabeled input image elements 615h-n may include or may have been derived from data collected using and received from one or more imaging systems 645 (e.g., the card reader as described with respect to the patient flow management system 100 of FIG. 1). The imaging systems 645 can include a system configured to collect image data (e.g., integrated camera). Thus, the classifier subsystems 610a-n able to consume new card examples into its training set and generate updated models automatically. This continuous learning capability effectively offsets the overall card variance problem. Moreover, labels associated with the training input image elements 615a-d and/or validation input image elements 615e-g may have been received or may be derived from data received from one or more provider systems 670, each of which may be associated with (for example) a physician, nurse, hospital, pharmacist, etc. associated with a particular subject. The received data may include (for example) one or more insurance cards corresponding to a particular patient. The insurance cards may be labeled with information such as insurance provider and member ID. The received data may further include the pixels of the locations of relevant information such as insurance provider and member ID within the one or more input image elements associated with the patient. In some instances, images of insurance cards that are input to one or more classifier subsystems 610a-n are received from the provider system 650. For example, the provider system 650 may receive images of insurance cards from the imaging system 645 and may then transmit the of insurance cards (e.g., along with a subject identifier and one or more labels) to the neural network system 605.

In some embodiments, data received at or collected at one or more of the imaging systems 645 may be aggregated with data received at or collected at one or more of the provider systems 650. For example, the neural network system 605 may identify corresponding or identical identifiers of a subject and/or time period so as to associate image data received from the imaging system 645 with label data received from the provider system 650. The neural network system 605 may further use metadata or automated image analysis to process data to determine to which classifier subsystem particular image data components are to be fed. For example, image data received from the imaging system 645 may correspond to insurance cards having only insurance provider information, only member ID information, or a combination thereof. Metadata, automated alignments and/or image processing may indicate, for each image, whether the insurance provider information and/or member ID information is included within the image. For example, automated alignments and/or image processing may include detecting whether an image has image properties corresponding to insurance provider information and/or member ID information. Label-related data received from the provider system 650 may be insurance provider information specific and/or member ID information specific. When label-related data is member ID information specific, metadata or automated analysis (e.g., using image analysis) can be used to identify to which location or region of an insurance card particular label-related data corresponds.

When label-related data is insurance provider information specific, identical label data (for a given provider) may be fed to each classifier subsystem during training.

In some embodiments, the computing environment 600 can further include a user device 655, which can be associated with a user that is requesting and/or coordinating performance of one or more iterations (e.g., with each iteration corresponding to one run of the model and/or one production of the model's output(s)) of the neural network system 605. The user may correspond to an administrator, insurance biller (e.g., associated with a medical laboratory), subject, medical professional, etc. Thus, it will be appreciated that, in some instances, the provider system 650 may include and/or serve as the user device 655. Each iteration may be associated with a particular subject (e.g., patient), who may (but need not) be different than the user. A request for the iteration may include and/or be accompanied with information about the particular subject (e.g., a name or other identifier of the subject, such as a de-identified patient identifier). A request for the iteration may include an identifier of one or more other systems from which to collect data, such as input image data that corresponds to the subject. In some instances, a communication from the user device 655 includes an identifier of each of a set of particular subjects, in correspondence with a request to perform an iteration for each subject represented in the set.

Upon receiving the request, the CNN system 605 can send a request (e.g., that includes an identifier of the subject) for unlabeled input image elements to the one or more corresponding imaging systems 645 and/or provider systems 650. The trained CNN models and/or RNN models can then process the unlabeled input image elements to classify an insurance card based on relevant information such as insurance provider, predict a location of relevant information on an insurance card such as member ID, predict text or strings of alphanumeric data on an insurance card, or a combination thereof. A result for each identified subject may include or may be based on the classifications or predictions from one or more CNN models and/or RNN models of the trained CNN models and/or RNN models deployed by the classifier subsystems 610a-n. For example, the predict text or strings of alphanumeric data on an insurance card output by a trained RNN model can include or may be based on output (e.g., a prediction a location of relevant information on an insurance card such as member ID) generated by the fully connected layer of one or more trained CNN models. One or more results (e.g., that include insurance card specific outputs and/or one or more subject specific outputs and/or processed versions thereof) may be transmitted to and/or availed to the user device 655. In some instances, some or all of the communications between the neural network system 605, imaging systems 645, provider systems 650, and user device 655 occur over communications network 660 (e.g., one or more local area networks (LAN) and/or one or more wide area networks (WAN)). In some instances, some or all of the communications between the neural network system 605 and the user device 655 over network 660 occurs via a user interface such as a website. It will be appreciated that the neural network system 605 may gate access to results, data and/or processing resources based on an authentication and/or authorization analysis.

While not explicitly shown, it will be appreciated that the computing environment 200 may further include a developer device associated with a developer. Communications from a developer device may indicate what types of input image elements are to be used for each of the CNN models and/or RNN models in the neural network system 605, a number of neural networks to be used, configurations of each neural network including number of hidden layers and hyperparameters, and how data requests are to be formatted and/or which training data is to be used (e.g., and how to gain access to the training data).

Figure 7:
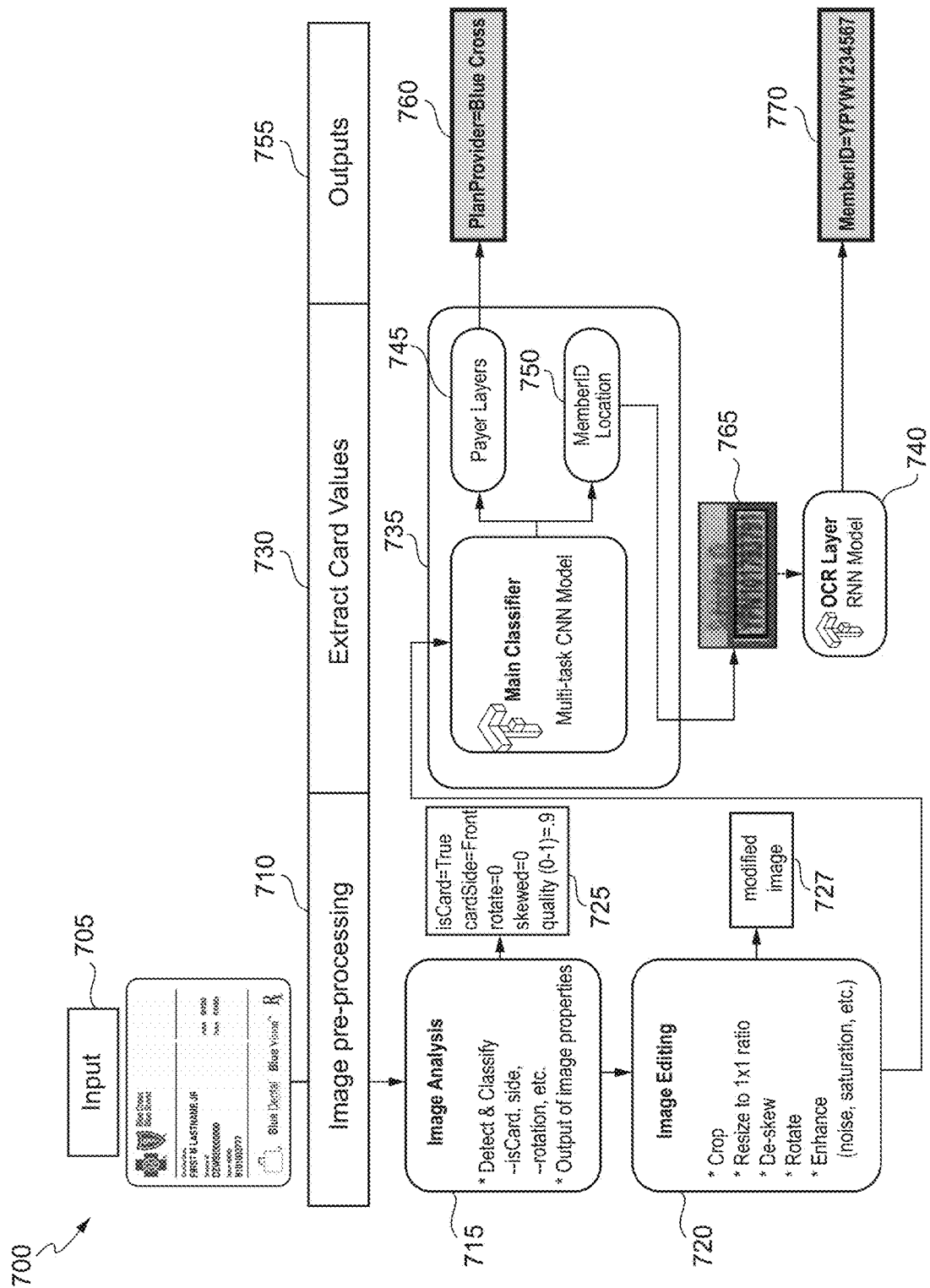
FIG. 7 shows an exemplary schematic diagram representative of a neural network architecture according to various embodiments.

FIG. 7 illustrates an exemplary schematic diagram 700 representative of a CNN and RNN architecture (e.g., a portion of the neural network system 605 described with respect to FIG. 6) for electronic insurance card data extraction in accordance with various embodiments. In some embodiments, input images 705 of insurance cards are obtained from an image source (e.g., the imaging systems 645 or provider systems 650, as described with respect to FIG. 6). The input images 705 may be structured as one or more arrays or matrices of pixel values. A given pixel position may be associated with (for example) a general intensity value and/or an intensity value as it pertains to each of one or more gray levels and/or colors (e.g., RGB values). Baseline input images 705 may be used as the input images into the CNN and RNN architecture. In some embodiments, the input images 705 are provided to pre-processing subsystem 710 of the CNN and RNN architecture. Pre-processing by the pre-processing subsystem 710 may include analysis by the image analysis module 715 and editing by the image editing module 720. The image analysis module 715 may be configured extract relevant features 725 (e.g., edges or sides of the card, rotation of the card, quality of the card, pixel data, etc.) detected within the input images 705 and/or modified input images 727. The image editing module may be configured to edit the input images 705 (e.g., crop, resize, de-skew, rotate, enhance, etc.) to generate modified input images 727.

Electronic insurance card data extraction may be performed in an extraction layer 730 comprising a multi-task CNN 735 and a RNN 740. In some embodiments, the multi-task CNN 735 comprises: (i) a first CNN model 745 for classification of an insurance card based on a first piece of information contained on the insurance card, and (ii) a second CNN model 750 for prediction of location of a second piece of information on the insurance card, where the first piece of information and the second piece of information are different pieces of information. In certain instances, the first piece of information is an insurance provider and the first CNN model 745 classifies the insurance card based on the insurance provider. The first piece of information is passed to the output layer 755 to be provided to a user as final output 760 (e.g., insurance card classification). In certain instances, the second piece of information is a member's identifier (e.g., member ID number/code) and the second CNN model 750 predicts a location of the member's identifier on the insurance card. The predicted location information is then used to extract or isolate image data 765 pertaining the second piece of information and share the extracted or isolated image data with the RNN 740 for further processing.

In various embodiments, each of the first CNN model 745 and the second CNN model 750 comprises an input layer, a hidden layer, and an output layer. Every hidden layer is connected to two layers: one from which the hidden layer receives a signal and one to which it passes the transformed signal. The input layer is connected to a subsequent layer (e.g., a hidden layer) and the output layer is connected to a prior layer (e.g., a hidden layer). The hidden layers may comprise one or more convolutional layers comprising one or more filters of feature masks to reduce the input and extract one or more features from the input image 705. The hidden layers may further comprise one or more pooling layers to move over the output of one or more convolutional layers (and optionally, a non-linearity layer such as a ReLu layer or Sigmoid layer) and make the output smaller. In some instances, the pooling is performed using a max pooling process and down-samples an input representation (image, hidden-layer output matrix, etc.) reducing its dimensionality and allowing for assumptions to be made about the features contained in the sub-regions binned. The hidden layers may further comprise one or more fully connected layers to classify the input images or features of the input images. The fully connected layers analyze the output of the previous layer (which should represent the activation maps of high level features) and determines which features most correlate to a particular class. For example, if the first CNN model 745 is classifying the insurance card as belonging to a certain insurance provider, it will have high values in the activation maps that represent high level features representative of the certain insurance provider. Similarly, if the second CNN 750 is predicting the location of a member ID on an insurance card, it will have high values in the activation maps that represent high level features representative of a member ID. Basically, a fully connected layer looks at what high level features most strongly correlate to a particular class and has particular weights so that when the algorithm computes the products between the weights and the previous layer, the model provides the correct probabilities for the different classes.

Multi-task learning is a general approach to learning related tasks using shared representation, with the aim of improving the performance of the overall machine-learning architecture. In order to capture the shared representation the first CNN model 745 and the second CNN model 750 are configured to share the output of one or more layers between the task of classifying the insurance card based on relative information such as insurance provider and the task of predicting a location of relative information such as a member ID. In some instances, the extracted features from one or more of the convolutional and pool layers are shared among the tasks and improve the performance of classifying the insurance card based on relative information such as insurance provider and predicting a location of relative information such as a member ID. In certain instances, the first CNN model 745 may comprise a first convolutional layer and first pooling layer that extract a first set of features specific to the task of classifying an insurance card based on a first piece of information, the second CNN model 750 may comprise a second convolutional layer and second pooling layer that extract a second set of features specific to the task of predicting a location of a second piece of information on the insurance card (the first piece of information being different from the second piece information). The first set of features and the second set of features may be used by a first fully connected layer of the first CNN model 745 to classify the insurance card and the first set of features and the second set of features are used by a second fully connected layer of the second CNN model 750 to predict the location of the second piece of information.

In some embodiments, the RNN 740 is trained on alphanumeric characters and comprises a stack with two or more recurring neural network layers configured to perform optical character recognition (OCR). The RNN 740 takes as input the extracted or isolated image data 755 that may contain text for the second piece of information and optionally the feature maps from the first CNN model 745 and the second CNN model 750. Based on the input, the RNN 740 generates a predicted sequence of alphanumeric characters corresponding to the text inside the extracted or isolated image data 755. In some instances, connectionist temporal classification loss may be used for further training. The predicted sequence of alphanumeric characters is passed to the output layer 755 to be provided to a user as final output 770 (e.g., member ID).

Figure 8:
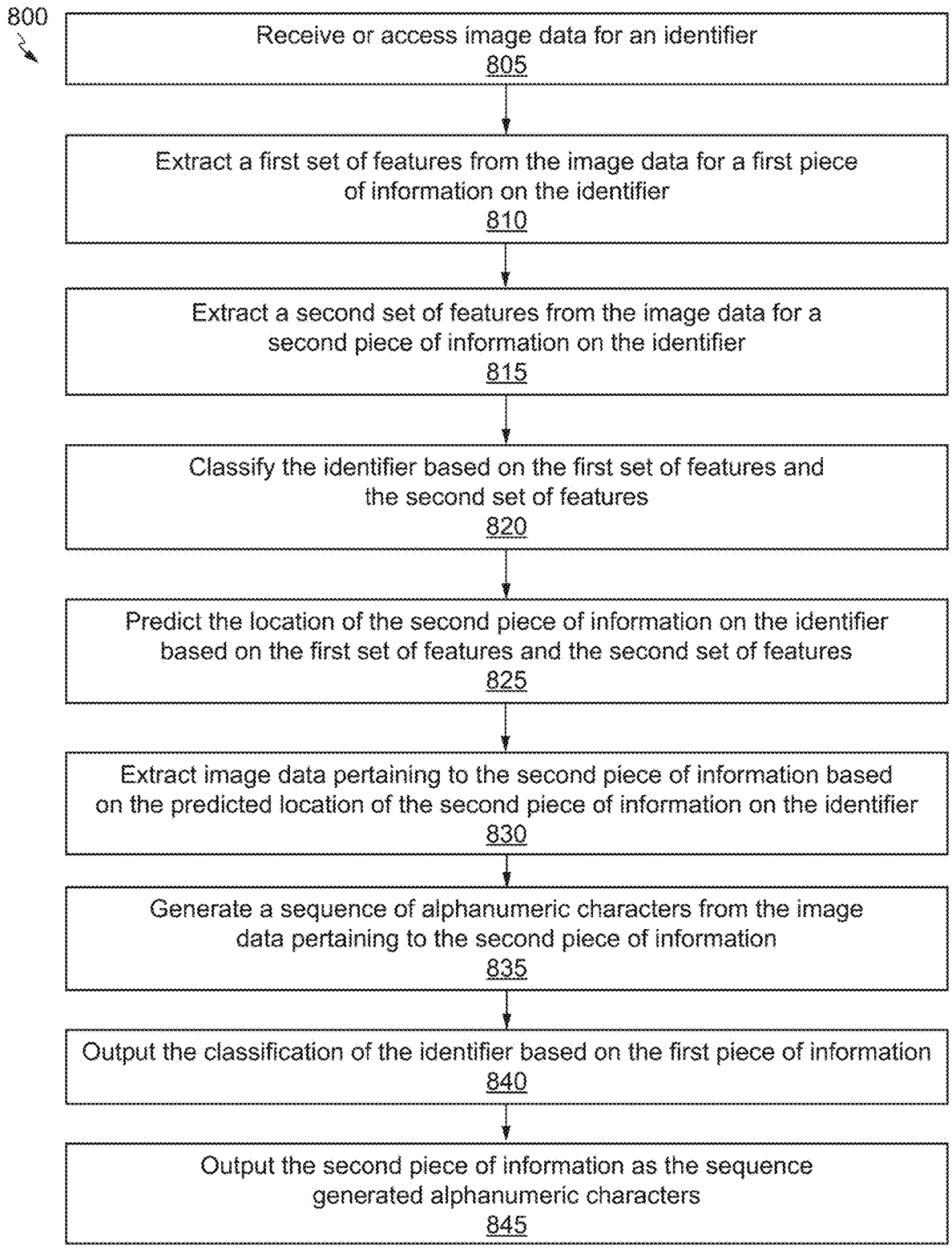
FIG. 8 shows an exemplary flow for insurance card recognition in accordance with various aspects of the invention.

FIG. 8 shows a process 800 for electronic insurance card data extraction in accordance with various embodiments. The process 800 begins at block 805, at which image data comprising an identifier for a subject is accessed or received. The identifier may be an insurance card such as a medical insurance card, and may comprise at least a first piece of information and/or a second piece of information. In certain instances, the first piece of information is an insurance provider and the second piece of information is a member's identifier (e.g., member ID number/code). Optionally, at block 810, the image data may be preprocessed to extract one or more features (e.g., edges or sides of the card, rotation of the card, quality of the card, pixel data, etc.) and/or edit the image data (e.g., crop, resize, de-skew, rotate, enhance, etc.) to generate modified image data.

At block 815, a first convolutional layer of a multi-task convolutional neural network model extracts a first set of features from the image data for a first piece of information on the identifier, where the first set of features are specific to a first task of classifying the identifier. At block 820, a second convolutional layer of the multi-task convolutional neural network model extracts a second set of features from the image data, where the second set of features are specific to a task of predicting a location of a second piece of information on the identifier. At block 825, a first fully connected layer of the multi-task convolutional neural network model classifies the identifier based on the first set of features and the second set of features. At block 830, a second fully connected layer of the multi-task convolutional neural network model predicts the location of the second piece of information on the identifier based on the first set of features and the second set of features. At block, 835, image data is extracted by the computing pertaining to the second piece of information based on the predicted location of the second piece of information on the identifier. At block 840, a recurrent neural network model generates a sequence of alphanumeric characters from the image data pertaining to the second piece of information. At block 845, the multi-task convolutional neural network outputs the classification of the identifier based on the first piece of information. At block 850, the recurrent neural network model outputs the second piece of information as the sequence of generated alphanumeric characters.

IV. Additional Considerations

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

What is claimed is:

1. A method comprising:

initiating, by a computing system in a distributed environment, a check-in process that includes prompting a user to scan an identifier;

receiving, by the computing system, image data from the scan of the identifier;

extracting, by a first convolutional layer of a first convolutional neural network model, a first set of features from the image data for a first piece of information on the identifier, wherein the first set of features are specific to a first task of classifying the identifier;

extracting, by a second convolutional layer of a second convolutional neural network model, a second set of features from the image data, wherein the second set of features are specific to a task of predicting a location of a second piece of information on the identifier and wherein the second convolutional neural network model is different from the first convolutional neural network model;

classifying, by a first fully connected layer of the first convolutional neural network model, the identifier based on the first set of features and the second set of features;

predicting, by a second fully connected layer of the second convolutional neural network model, the location of the second piece of information on the identifier based on the first set of features and the second set of features;

extracting, by the computing system, image data pertaining to the second piece of information based on the predicted location of the second piece of information on the identifier;

generating, by a recurrent neural network model, a sequence of alphanumeric characters from the image data pertaining to the second piece of information;

outputting, by the multi-task convolutional neural network, the classification of the identifier based on the first piece of information; and outputting, by the recurrent neural network model, the second piece of information as the sequence of generated alphanumeric characters.

2. The method of claim 1, wherein the identifier is an insurance card, the first piece of information is an insurance provider, and the second piece of information is a member identifier.

3. The method of claim 1, further comprising:
determining, by the computing system, whether the user is known user based on the second piece of information;
when the user is a known user, verifying, by the computing system, user data saved in the computing system associated with the identifier;
once the user data is verified, determining, by the computing device, whether the user has an outstanding balance for prior services;
when the user does not have the outstanding balance, determining, by the computing device, whether the user has a scheduled appointment; and
when the user has a scheduled appointment, checking the user in for the scheduled appointment.

4. The method of claim 1, further comprising when the user is not the known user, initiating, by the computing system, a registration process that includes requesting demographic information from the user and prompts the user to accept terms and conditions for scheduling services via the computing system.

5. The method of claim 1, further comprising:
when the user does not have a scheduled appointment or after accepting the terms and conditions for scheduling the services via the computing system, displaying, by the computing system, a list of services currently available for appointment, and prompting the user to select one or more services for scheduling;
upon receiving the selection of the one or more services, displaying, by the computing system, a list of times currently available for having the one or more services performed, and prompting the user to select a time for scheduling; and
upon receiving the selection of the time, generating, by the computing system, an appointment for the services at the selected time.

6. The method of claim 1, further comprising when the user does have the outstanding balance, prompting, by the computing device, the user to pay the outstanding balance or a portion of the outstanding balance.

7. A non-transitory machine readable storage medium having instructions stored thereon that when executed by one or more processors cause the one or more processors to perform operations comprising:
initiating a check-in process that includes prompting a user to scan an identifier;
receiving image data from the scan of the identifier;
extracting, by a first convolutional layer of a first convolutional neural network model, a first set of features from the image data for a first piece of information on the identifier, wherein the first set of features are specific to a first task of classifying the identifier;
extracting, by a second convolutional layer of a second convolutional neural network model, a second set of features from the image data, wherein the second set of features are specific to a task of predicting a location of a second piece of information on the identifier and wherein the second convolutional neural network model is different from the first convolutional neural network model;
classifying, by a first fully connected layer of the first convolutional neural network model, the identifier based on the first set of features and the second set of features;
predicting, by a second fully connected layer of second convolutional neural network model, the location of the second piece of information on the identifier based on the first set of features and the second set of features;
extracting image data pertaining to the second piece of information based on the predicted location of the second piece of information on the identifier;
generating, by a recurrent neural network model, a sequence of alphanumeric characters from the image data pertaining to the second piece of information;
outputting, by the multi-task convolutional neural network, the classification of the identifier based on the first piece of information; and
outputting, by the recurrent neural network model, the second piece of information as the sequence of generated alphanumeric characters.

8. The non-transitory machine readable storage medium of claim 7, wherein the identifier is an insurance card, the first piece of information is an insurance provider, and the second piece of information is a member identifier.

9. The non-transitory machine readable storage medium of claim 7, wherein the operations further comprise:
determining whether the user is known user based on the second piece of information;
when the user is a known user, verifying user data saved in the computing system associated with the identifier;
once the user data is verified, determining whether the user has an outstanding balance for prior services;
when the user does not have the outstanding balance, determining whether the user has a scheduled appointment; and
when the user has a scheduled appointment, checking the user in for the scheduled appointment.

10. The non-transitory machine readable storage medium of claim 7, wherein the operations further comprise when the user is not the known user, initiating, by the computing system, a registration process that includes requesting demographic information from the user and prompts the user to accept terms and conditions for scheduling services via the computing system.

11. The non-transitory machine readable storage medium of claim 7, wherein the operations further comprise:
when the user does not have a scheduled appointment or after accepting the terms and conditions for scheduling the services via the computing system, displaying, by the computing system, a list of services currently available for appointment, and prompting the user to select one or more services for scheduling;
upon receiving the selection of the one or more services, displaying, by the computing system, a list of times currently available for having the one or more services performed, and prompting the user to select a time for scheduling; and
upon receiving the selection of the time, generating, by the computing system, an appointment for the services at the selected time.

12. The non-transitory machine readable storage medium of claim 7, wherein the operations further comprise when the user does have the outstanding balance, prompting, by the computing device, the user to pay the outstanding balance or a portion of the outstanding balance.

13. A system comprising:
a memory configured to store computer-executable instructions; and
a processor configured to access the memory and execute the computer-executable instructions to perform operations comprising:
initiating a check-in process that includes prompting a user to scan an identifier;
receiving image data from the scan of the identifier;
extracting, by a first convolutional layer of a first convolutional neural network model, a first set of features from the image data for a first piece of information on the identifier, wherein the first set of features are specific to a first task of classifying the identifier;
extracting, by a second convolutional layer of a second convolutional neural network model, a second set of features from the image data, wherein the second set of features are specific to a task of predicting a location of a second piece of information on the identifier and wherein the second convolutional neural network model is different from the first convolutional neural network model;
classifying, by a first fully connected layer of the first convolutional neural network model, the identifier based on the first set of features and the second set of features;
predicting, by a second fully connected layer of the second convolutional neural network model, the location of the second piece of information on the identifier based on the first set of features and the second set of features;
extracting image data pertaining to the second piece of information based on the predicted location of the second piece of information on the identifier;
generating, by a recurrent neural network model, a sequence of alphanumeric characters from the image data pertaining to the second piece of information;
outputting, by the multi-task convolutional neural network, the classification of the identifier based on the first piece of information; and
outputting, by the recurrent neural network model, the second piece of information as the sequence of generated alphanumeric characters.

14. The system of claim 13, wherein the identifier is an insurance card, the first piece of information is an insurance provider, and the second piece of information is a member identifier.

15. The system of claim 13, wherein the operations further comprise:
determining whether the user is known user based on the second piece of information;
when the user is a known user, verifying user data saved in the computing system associated with the identifier;
once the user data is verified, determining whether the user has an outstanding balance for prior services;
when the user does not have the outstanding balance, determining whether the user has a scheduled appointment; and
when the user has a scheduled appointment, checking the user in for the scheduled appointment.

16. The system of claim 13, wherein the operations further comprise when the user is not the known user, initiating, by the computing system, a registration process that includes requesting demographic information from the user and prompts the user to accept terms and conditions for scheduling services via the computing system.

17. The system of claim 13, wherein the operations further comprise:
when the user does not have a scheduled appointment or after accepting the terms and conditions for scheduling the services via the computing system, displaying, by the computing system, a list of services currently available for appointment, and prompting the user to select one or more services for scheduling;
upon receiving the selection of the one or more services, displaying, by the computing system, a list of times currently available for having the one or more services performed, and prompting the user to select a time for scheduling; and
upon receiving the selection of the time, generating, by the computing system, an appointment for the services at the selected time.

18. The system of claim 13, wherein the operations further comprise when the user does have the outstanding balance, prompting, by the computing device, the user to pay the outstanding balance or a portion of the outstanding balance.

* * * * *